United States Patent [19]
Gamble et al.

[11] Patent Number: 5,874,554
[45] Date of Patent: Feb. 23, 1999

[54] METHODS AND SOLVENT VEHICLES FOR REAGENT DELIVERY IN OLIGONUCLEOTIDE SYNTHESIS USING AUTOMATED PULSE JETTING DEVICES

[75] Inventors: Ronald C. Gamble, Altadena; Thomas P. Theriault, Manhattan Beach; Scott C. Winder, Altadena, all of Calif.

[73] Assignee: Incyte Pharmaceuticals, Inc., Palo Alto, Calif.

[21] Appl. No.: 767,233

[22] Filed: Dec. 13, 1996

[51] Int. Cl.$^6$ .............................. C07H 19/00; C08G 63/48
[52] U.S. Cl. .......................... 536/22.1; 536/25.3; 525/50; 525/53; 525/54.2
[58] Field of Search .................. 536/22.1, 25.3; 525/50, 53, 54.2

[56] References Cited

U.S. PATENT DOCUMENTS

| | | | |
|---|---|---|---|
| 4,458,066 | 7/1984 | Caruthers et al. | 536/27 |
| 4,517,338 | 5/1985 | Urdea et al. | 525/54.11 |
| 4,661,450 | 4/1987 | Kempe et al. | 435/172.3 |
| 4,877,745 | 10/1989 | Hayes et al. | 436/166 |
| 4,990,517 | 2/1991 | Peterson et al. | 514/300 |
| 5,286,715 | 2/1994 | Vranesic et al. | 514/18 |
| 5,462,748 | 10/1995 | Lloyd et al. | 424/484 |

FOREIGN PATENT DOCUMENTS

| | | |
|---|---|---|
| 0035255 | 9/1981 | European Pat. Off. . |
| 0617047A1 | 9/1994 | European Pat. Off. . |
| WO 94/01215 | 1/1994 | WIPO . |

OTHER PUBLICATIONS

Itakura, K. et al., "Synthesis and Use of Synthetic Oligonucleotides" *Annu.Rev.Biochem.* (1984) 53:323–356.

Narang, Saran A., "DNA Synthesis" *Tetrahedron* (1983) 39:3–22.

Stryer, Lubert A., "DNA Probes and Genes Can Be Synthesized By Automated Solid–Phase Methods" *Biochmistry*, (1988) 6:123–124.

Schena, M. et al., "Quantitative Monitoring of Gene Expression Patterns with a Complementary DNA Microarray." *Science* (1995) 270:467–470.

Kozal, M.J. et al., "Extensive polymorphisms observed in HIV–1 clade B protease gene using high–density oligonucleotide arrays" *Nature Medicine* (1996) 2:753–759.

*Primary Examiner*—Ardin H. Marschel
*Assistant Examiner*—Jezia Riley
*Attorney, Agent, or Firm*—Incyte Pharmaceuticals, Inc.

[57] ABSTRACT

Solvent vehicles and methods of their use in the pulse jet delivery of reagents in automated oligonucleotide synthesis by the solid-phase phosphoramidite method are provided. For pulse jet delivery of the activated monomer, acetonitrile in combination with at least one stabilizer co-solvent is employed as the solvent vehicle, where the stabilizer co-solvent is an inert, organic solvent having a boiling point of at least 100° C. For pulse jet delivery of the detritylation reagent, a mono- or disubstituted methane is employed as the solvent vehicle, where substituents have a molecular weight greater than 36 daltons. Use of the solvent vehicles according to the subject invention provides for reduced reagent precipitation in the pulse jet tubes and improved results.

33 Claims, No Drawings

METHODS AND SOLVENT VEHICLES FOR REAGENT DELIVERY IN OLIGONUCLEOTIDE SYNTHESIS USING AUTOMATED PULSE JETTING DEVICES

The United States Government may have certain rights in the present invention under an ATP/NIST grant.

INTRODUCTION

1. Field of the Invention

The field of this invention is solid phase oligonucleotide synthesis.

2. Background

Chemical oligonucleotide synthesis has advanced to the point where nearly all such synthesis is carried out with highly automated machines. The chemistry employed in such machines is known as the phosphoramidite solid-phase synthesis method and is described in detail in Itakura et al, "Synthesis and Use of Synthetic Oligonucleotides," Annu. Rev. Biochem. (1984) 53:323 and Narang et al., "DNA Synthesis," Tetrahedron (1983) 39:3. Generally, this method comprises three repetitive steps: (1) a coupling step; (2) an oxidation step; and (3) a detritylation step. In the coupling step, an activated protonated deoxyribonucleoside 3'-phosphoramidite monomer having a dimethoxytrityl blocking group at the 5' position is contacted with a solid phase bound nucleoside. The activated monomer is typically present in acetonitrile. Contact results in joining of the activated monomer to the 5'OH of the solid phase bound nucleoside through a phosphite triester group. In the oxidation step, the phosphite triester is oxidized to a phosphotriester, usually through contact with $I_2$. Finally, in the detritylation step, the dimethoxytrityl protecting group on the newly added activated monomer is removed with a detrylation reagent, e.g. di- or trichloroacetic acid. The detritylation reagent is typically present in dichloromethane. Through appropriate repetition of the above steps, an oligonucleotide of desired length and sequence can be synthesized. This method is described in greater detail in U.S. Pat. No. 4,458,066; as well as in "Oligonucleotide Synthesis-A Practical Approach" (Gait, IRL Press)(1984) and Stryer, Biochemistry (1988) pp 123–124.

Because of the repetitive nature of the above synthesis method, the method is particularly suited for automation, in which the above steps are automatically performed. A variety of automated oligonucleotide synthesis devices capable of synthesizing oligonucleotides according to the phosphoramidite method have been developed. See, for example, WO 94/01215. In the area of oligonucleotide synthesis, miniaturization of automated synthesis devices has become a desirable goal for a variety of reasons, e.g. to reduce reagent waste, etc. One class of devices that have been developed to meet this goal are pulse jetting devices capable of delivering less than 1 $\mu$l spots in a reproducible fashion on the surface of a substrate. Such devices provide for the possibility of producing microarrays of oligonucleotides, which microarrays are finding use in new assay applications. See Schena et al., "Quantitative Monitoring of Gene Expression Patterns with a Complementary DNA Microarray," Science (1995) 270:467–470 and Kozal et al., "Extensive Polymorphisms Observed in HIV-1 Clade B Protease Gene Using High-Density Oligonucleotide Arrays," Nature Medicine (1996) 2:753–759.

Despite the promise of automated oligonucleotide synthesis with pulse jetting devices, certain obstacles resulting from the chemistry involved in the synthesis must be overcome. For example, although acetonitrile provides for high efficiency in the coupling reaction, when used in a pulse jetting device it tends to evaporate rapidly from the jetting tube, resulting in activated monomer precipitation and concomitant plugging of the jetting tube orifice. Likewise, dichloromethane can lead to detritylation reagent precipitation and plugging of the tube orifice.

Since reagent precipitation and orifice plugging result in reagent waste and time consuming cleaning steps, there is interest in the identification of new solvent vehicles for use in reagent delivery through pulse jetting devices. The new solvent vehicles should at least reduce, if not substantially eliminate, reagent precipitation orifice plugging. Ideally, such solvent vehicles should be compatible with the particular synthesis reaction being performed, e.g coupling or detritylation, so as not to detract from the efficiency of the synthesis.

Relevant Literature

U.S. Pat. No. 4,877,745 discloses a reagent fluid dispensing apparatus comprising a jetting tube mounted within a cylindrical piezo-electric transducer, and reports the use of glycerin in reagent solvent vehicles to reduce the problems associated with solvent evaporation.

SUMMARY OF THE INVENTION

Solvent vehicles for use in the delivery of reagents during oligonucleotide synthesis with an automated pulse jetting device are provided. For pulse jet delivery of the activated monomer, acetonitrile is combined with a stabilizer co-solvent to produce an anhydrous activated monomer solvent vehicle, where the stabilizer co-solvent is an inert organic solvent having a boiling point or flash point greater than about 100° C. For delivery of the detritylation reagent, a mono-or disubstituted methane, where the substituent has a molecular weight greater than 36 daltons, is employed as the detritylation reagent solvent vehicle, which solvent vehicle may further comprise an additional co-solvent. Use of the particular solvent vehicles according to the subject invention provides for at least reduced reagent precipitation in the pulse jet delivery device.

DESCRIPTION OF THE SPECIFIC EMBODIMENTS

Solvent vehicles, and methods of their use, in the pulse jet delivery of reagents in automated oligonucleotide synthesis by the solid-phase phosphoramidite method are provided. Specifically, a solvent vehicle comprising acetonitrile in combination with an organic stabilizing co-solvent having a boiling point or flash point greater than about 100° C. is employed for pulse jet delivery of the activated phosphoramidite monomer in the coupling step. For the detritylation step, the detritylation reagent is delivered in a solvent vehicle that provides for reduced reagent precipitation, where the solvent vehicle may comprise a co-solvent.

As mentioned above, the subject solvent vehicles are suitable for the pulse jet delivery of reagents necessary for oligonucleotide synthesis by the phosphoramidite method, as described in the background section above.

The automated oligonucleotide synthetic devices in which the subject solvent vehicles find use are those devices in which the reagents are delivered to a substrate by pulse jetting. Generally, such devices comprise a reagent tube, e.g. a capillary, having an orifice at one end. Associated with the tube in the region of the orifice is a transducer means, such as a piezoelectric device or heating element, which forces a defined volume of liquid reagent out of the tube through orifice upon activation. Pulse jetting devices which are adaptable for use in the synthesis of oligonucleotides according to the solid phase phosphoramidite method and in which the subject solvent vehicles find use include the devices disclosed in WO 94/01215 and U.S. patent application Ser. No. 08/646,535, the disclosures of which are herein incorporated by reference.

For the pulse jet delivery of activated monomers in the coupling step according to the subject invention, the activated monomer solvent delivery vehicles are anhydrous and comprise acetonitrile in combination with at least one, usually not more than three, more usually not more than two different co-solvents or stabilizers which serve to at least reduce the level of, if not substantially inhibit, precipitation of the activated monomer in the pulse jet tube. The stabilizer will be an organic solvent having a boiling point or flash point of greater than about 100° C., usually greater than about 120° C., and more usually greater than about 150° C. The molecular weight of the stabilizing solvent will generally range from about 70 to 200 daltons, usually from about 80 to 140 daltons. The organic solvent employed as the stabilizer should be: 1) be miscible with acetonitrile, 2) not precipitate the solutes, 3) be non-reactive with chemistry at hand, 4) reduce the apparent vapor pressure of acetonitrile in the vicinity of the orifice (or, in any event, to allow for reliable jetting), and, yet, 5) not affect the chemistry on the surface, i.e., allow for the linking chemistry to occur and evaporation of the droplet before the rinse cycle. The most likely co-solvents which satisfies these considerations are solvents that are related structurally to acetonitrile, but exhibit lower vapor pressure (as would be expected from compounds having high boiling points, or flash points—if boiling points are not available). With these considerations in mind, we have identified which exhibit improved jetting. These co-solvents and their properties are set forth in Table 1.

TABLE 1

ACCEPTABLE CO-SOLVENTS

| CO-SOLVENT | ACRONYM | Molecular Weight | Boiling Point | Flash Point |
|---|---|---|---|---|
| Trimehtyl-phosphate | TMP | 140 daltons | 197° C. | |
| Methyl-Pyrroleaceto-nitrile | N-MPACN | 120 daltons | | >110° C. |
| Methyl-Pyrrolidinone | N-MPN | 99 daltons | 202° C. | |
| n,n,-Dimethyl Foramide | DMF | 73 daltons | 153° C. | |
| Nitromethane | | 61 daltons | 101° C. | |

Organic solvents of interest as stabilizers will generally have from 2 to 8 carbon atoms, more usually 3 to 7 carbon atoms, with 1 or more heteroatoms, usually 2 to 5 heteroatoms, where the heteroatoms are typically O, N or P, where the stabilizing solvent may be cyclic, where N may be an annular atom, and will generally have from 1 to 3 methyl groups and no hydroxy groups. Specific stabilizing solvents of interest include: amides, such as dimethyl formamide; phosphates, such as trimethyl phosphate; pyrroles, such as N-methyl pyrrolidinone and N-methyl pyrroleacetonitrile; and the like.

The amount of stabilizer employed in the activated monomer solvent vehicle will be sufficient to reduce the volatility of the vehicle and thereby reduce or substantially eliminate reagent precipitation in the jetting tube. Generally, the amount of stabilizer will range from about 2 to 10% (v/v) of the vehicle, usually from about 2.5 to 10% (v/v) and more usually 4 to 6% (v/v) of the vehicle. Where either trimethyl phosphate or pyrroles, such as N-methyl-pyrrolidinone and N-methyl-pyrroleacetonitrile, are employed as the stabilizer, the amount of stabilizer will range from about 2.5 to 7.5% (v/v), and will preferably be 5% (v/v) of the co-solvent vehicle. Where dimethyl formamide is employed as the stabilizer, the amount of stabilizer in the co-solvent vehicle will range from about 2.5 to 10% (v/v), but will preferably be 5% (v/v) of the co-solvent vehicle.

For pulse jet delivery of the detritylation reagent according to the subject invention, a detritylation reagent solvent delivery vehicle will be employed in which reagent precipitation in the jet tube is slowed or prevented. The detritylation reagent will typically be zinc bromide or trichloroacetic acid. Solvent vehicles finding use include mono- and disubstituted methanes, where the substituents will have molecular weights greater than about 36 daltons. In the monosubstituted methanes, the substituent is preferably a nitro group while in the disubstituted methanes, the substituents are preferably halo groups having an atomic number greater than 17, where bromine is preferred. Where zinc bromide is employed as the detritylation reagent, a solvent vehicle saturated with zinc bromide is typically used, where the solvent vehicle is nitromethane alone or in combination with at least one additional co-solvent, where the volume ratio of nitromethane to co-solvent will range from 8.5:1 to 9.5:1, and will preferably be 9:1, where the co-solvent will be a lower alkanol or diol, usually having no more than about 10 carbon atoms, more usually no more than about 8 carbon atoms, and usually more than 2 carbon atoms, where tetraethylene glycol and butanol are preferred. Where trichloroacetic acid is employed as the detritylation agent, the solvent vehicle will preferably be dibromomethane, where the volume % of trichloracetic acid in the dibromomethane solvent vehicle will range from about 0.001 to 0.01.

The following examples are offered by way of illustration and not by way of limitation.

EXPERIMENTAL

An array of oligonucleotides was synthesized using the pulse jetting device described in U.S. patent application Ser. No. 08/646,535, the disclosure of which is herein incorporated by reference. For pulse jet delivery of the activated phosphoramidite monomer, the following four solvent vehicles were employed:

(a) acetonitrile in combination with 5% (v/v) N-methyl-pyrrolidinone
(b) acetonitrile in combination with 5% (v/v) dimethyl formamide
(c) acetonitrile in combination with 5% (v/v) trimethyl phosphate
(d) acetonitrile in combination with 5% (v/v) N-methyl-pyrroleacetonitrile For pulse jet delivery of the detritylation reagent, the following solvent vehicles were employed:

| Detritylation Reagent | Solvent Vehicle |
|---|---|
| ZnBr$_2$ (saturated) at 9:1 | nitromethane:tetraethylene glycol |
| ZnBr$_2$ (saturated) | nitromethane:butanol at 9:1 |

-continued

| Detritylation Reagent | Solvent Vehicle |
|---|---|
| Trichloroacetic Acid (0.001 to 0.01%) | dibromomethane |

With each of the above solvent vehicles listed above, it was found that the reagents were soluble in the vehicle, the vehicle did not adversely affect the efficiency of the reaction, either coupling or detritylation, and reagent precipitation did not occur, even when there were extended periods of non-use.

It is evident from the above results and discussion that solvent vehicles particularly suited for the pulse jet delivery of reagents for synthesis of oligonucleotides by the solid-phase phosphoramidite method are provided. The use of the subject solvent vehicles at least reduces, if not substantially eliminates, reagent precipitation in the jetting tubes, and yet do not detract from the efficiency of the particular reactions occurring during the synthesis. By preventing reagent precipitation, the subject solvent vehicles provide for improved results using automated pulse jetting devices.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. In a method of chemically synthesizing oligonucleotides according to the solid-phase phosphoramidite method using a pulse jet automated synthesis device, the improvement comprising:

pulse jet delivering activated phosphoramidite monomers in a solvent vehicle comprising acetonitrile in combination with at least one stabilizing co-solvent, wherein said stabilizing co-solvent is an organic solvent having a boiling point or flash point greater than about 100° C., and further wherein said stabilizing co-solvent is miscible with acetonitrile.

2. The method according to claim 1, wherein said stabilizing co-solvent has from 2 to 8 carbon atoms.

3. The method according to claim 1, wherein said stabilizing co-solvent has a molecular weight ranging from about 50 to 200 daltons.

4. The method according to claim 1, wherein said stabilizing co-solvent is selected from the group consisting of amides, phosphates and pyrroles.

5. The method according to claim 1, wherein said improvement further comprises pulse jet delivering a detritylation reagent in a detritylation reagent solvent vehicle comprising a mono- or disubstituted methane, wherein substituents of said methane have a molecular weight of greater than 36 daltons.

6. The method according to claim 5, wherein said detritylation reagent is selected from the group consisting of zinc bromide and trichloroacetic acid.

7. The method according to claim 6, wherein said mono- or disubstituted methane is selected from the group consisting of nitromethane and dibromomethane.

8. The method according to claim 6, wherein said detritylation reagent is zinc bromide and said detritylation reagent solvent vehicle comprises nitromethane in combination with at least one additional co-solvent.

9. The method according to claim 8, wherein said additional co-solvent is an alkanol or diol of from 4 to 8 carbon atoms.

10. The according to claim 6, wherein said detritylation reagent is trichloroacetic acid and said detritylation reagent solvent vehicle is dibromomethane.

11. The method according to claim 1, wherein said stabilizing co-solvent is an amide, phosphate or pyrrole, and wherein the improvement further comprises:

pulse jet delivering a detritylation reagent in a detritylation reagent solvent vehicle comprising a mono- or disubstituted methane, wherein substituents of said mono- or disubstituted methane have a molecular weight greater than 36 daltons.

12. The method according to claim 11, wherein said detritylation reagent is zinc bromide or trichloroacetic acid.

13. The method according to claim 12, wherein said mono- or disubstituted methane is selected from the group consisting of nitromethane and dibromomethane.

14. The method according to claim 13, wherein said detritylation reagent is zinc bromide and said detritylation reagent solvent vehicle comprises nitromethane in combination with at least one additional co-solvent.

15. The method according to claim 14, wherein said additional co-solvent is an alkanol or diol of from 4 to 8 carbon atoms.

16. The method according to claim 15, wherein said additional co-solvent is selected from the group consisting of tetraethylene glycol and butanol.

17. The method according to claim 12, wherein said detritylation reagent is trichloroacetic acid and said detritylation reagent solvent vehicle is dibromomethane.

18. The method according to claim 1, wherein said stabilizing co-solvent is selected from the group consisting of N-methyl-pyrrolidinone, dimethyl formamide, trimethyl phosphate and N-methyl-pyrroleacetonitrile, and wherein the improvement further comprises:

pulse jet delivering a detritylation reagent in a detritylation reagent solvent vehicle comprising a mono- or disubstituted methane, wherein substituents of said mono- or disubstituted methane have a molecular weight greater than 36 daltons, wherein said mono- or disubstituted methane is a selected from the group consisting of nitromethane or dibromomethane.

19. The method according to claim 18, wherein said pulse jetting is with a piezoelectric dispenser.

20. The method according to claim 18, wherein said pulse jetting is with a bubble jet dispenser.

21. A solvent vehicle for use in the pulse jet delivery of deoxyribonucleoside 3'-phosphoramidites, said solvent vehicle comprising acetonitrile in combination with at least one stabilizing co-solvent, wherein said organic stabilizing co-solvent has a boiling or flash point greater than 100° C., and further wherein said stabilizing co-solvent is miscible with acetonitrile.

22. The solvent vehicle according to claim 21, wherein said stabilizing co-solvent has from 2 to 8 carbon atoms.

23. The solvent vehicle according to claim 21, wherein said stabilizing co-solvent is an amide, phosphate or pyrrole.

24. The solvent vehicle according to claim 23, wherein said stabilizing co-solvent is from 2.5 to 10% (v/v) of said solvent vehicle.

25. The solvent vehicle according to claim 24, wherein said stabilizing co-solvent is N-methyl pyrrolidinone.

26. The solvent vehicle according to claim 24, wherein said stabilizing co-solvent is dimethyl formamide.

27. The solvent vehicle according to claim 24, wherein said stabilizing co-solvent is trimethyl phosphate.

28. The solvent vehicle according to claim 24, wherein said stabilizing co-solvent is N-methyl pyrroleacetonitrile.

29. A detritylation reagent solvent vehicle for use in the pulse jet delivery of a detritylation reagent, said detritylation reagent solvent vehicle comprising a mono- or disubstituted methane, wherein substituents of said mono- or disubstituted methane have a molecular weight greater than 36 daltons, and further wherein said detritylation reagent solvent vehicle is delivered in conjunction with pulse jet delivery of a solvent vehicle comprising acetonitrile in combination with at least one stabilizing co-solvent, wherein said stabilizing co-solvent is an organic solvent having a boiling point or flash point greater than about 100° C. and further wherein said stabilizing co-solvent is miscible with acetonitrile.

30. The detritylation reagent solvent vehicle according to claim 29, wherein said mono- or disubstituted methane is selected from the group consisting of nitromethane and dibromomethane.

31. The detritylation reagent solvent vehicle according to claim 30, wherein said detritylation reagent is zinc bromide and said detritylation reagent solvent vehicle comprises nitromethane in combination with at least one additional co-solvent.

32. The detritylation reagent solvent vehicle according to claim 31, wherein said additional co-solvent is an alkanol or diol of from 4 to 8 carbon atoms.

33. The detritylation reagent solvent vehicle according to claim 29, wherein said detritylation reagent is trichloroacetic acid and said detritylation reagent solvent vehicle is dibromomethane.

* * * * *